United States Patent [19]

Bradcovich et al.

[11] 4,426,578
[45] Jan. 17, 1984

[54] SUPPORT STRUCTURE FOR ROTATABLE SCINTILLATION DETECTOR

[75] Inventors: James M. Bradcovich, Akron; Robert H. Wake, Solon; Richard M. Kovacs, Jr.; Carlos D. Pinkstaff, both of Chardon, all of Ohio

[73] Assignee: Technicare Corporation, Solon, Ohio

[21] Appl. No.: 195,269

[22] Filed: Oct. 8, 1980

[51] Int. Cl.³ .............................................. G01T 1/20
[52] U.S. Cl. .................................. 250/363 S; 378/15; 378/17
[58] Field of Search ........................ 250/363 S, 445 T; 269/56, 71, 908; 378/15, 17

[56] References Cited

U.S. PATENT DOCUMENTS

| | | |
|---|---|---|
| 1,599,696 | 9/1926 | Wantz . |
| 2,595,260 | 5/1952 | Hollstein . |
| 3,281,598 | 10/1966 | Hollstein . |
| 3,617,749 | 11/1971 | Masslot . |
| 3,697,751 | 10/1972 | Tschunt . |
| 3,756,549 | 9/1973 | Lange . |
| 3,845,308 | 10/1974 | Cattrell . |
| 4,064,441 | 12/1977 | Casale ............................... 250/363 S |
| 4,150,297 | 4/1979 | Borggren . |
| 4,216,381 | 8/1980 | Lange ............................... 250/363 S |
| 4,223,222 | 9/1980 | Gray et al. ....................... 250/363 S |

FOREIGN PATENT DOCUMENTS 1175032 12/1969 United Kingdom .
1572809 8/1980 United Kingdom .

OTHER PUBLICATIONS

Dymax LF Gamma Camera by Elscint, Inc., Hackensack, NJ 07602.
The Flexible Concept in Gamma Cameras, The XL-91 Detector Raytheon Medical Electronics, 70 Ryan St., Stamford, CT 06907.
Pho/Gamma LFOV Large Field of View Scintillation Camera Searle Radiographics, Inc.
DynaCamera 4, Picker Corporation, 595 Miner Road, Cleveland, OH 44143.
MaxiCamera 400 T, General Electric.
Sigma 400, Sigma 410S and Sigma 438, Technicare Corporation, 29100 Aurora Road, Solon, OH 44139.

Primary Examiner—Janice A. Howell
Attorney, Agent, or Firm—Michael A. Kaufman

[57] ABSTRACT

A curved beam apparatus adapted for mounting thereon a scintillation detector. The apparatus comprises a circular C-arm which is balanced with a counterweight at one end and a scintillation detector pivotally mounted by means of a yoke at the other end. The C-arm is mounted in a carrier member which in turn is attached to a base. The carrier member is rotatable about an axis passing through its center. In addition, the C-arm rotates circumferentially along a plane defined by the shape of the C-arm and intersecting said axis. The combination of the rotation of the C-arm and the rotation of the carrier member permits the scintillation detector to be quickly and easily manually positioned to any desired location on an imaginary sphere surrounding a portion of patient to be examined.

17 Claims, 12 Drawing Figures

SUPPORT STRUCTURE FOR ROTATABLE SCINTILLATION DETECTOR

TECHNICAL FIELD

This invention relates to a stand for a gamma or scintillation detector and more particularly to a curved beam apparatus therefor.

BACKGROUND ART

In the field of nuclear medicine, there are a variety of radioisotope cameras to accomodate various types of diagnostic studies. In addition to a variety of camera types, there are a range of available detectors as well as stands on which the detectors are mounted and positioned.

As is well known, a scintillation camera produces an image on a cathode ray tube from the gamma rays emitted by the radionuclide introduced into the patient to be examined. The gamma ray or scintillation detector portion of the camera absorbs incoming gamma rays that penetrate the crystal of the detector. In the detector there is provided in front of the crystal a collimator which permits passage of only those gamma rays that travel essentially parallel to the axis of the holes of the collimator that pass through to the crystal. Since in different studies, different portions of a patient are required to be diagnosed, or alternatively different portions of the patient are needed to be consecutively studied, it is important that the detector can be quickly and easily positioned in the proper orientation at the desired location with a minimum of inconvenience to the patient and ease to the operator.

Regardless of the way this is accomplished, since the detector must be located to a specific point in space, there are three spatial coordinates to be concerned with, in addition to a specific tilting of the detector at that spatial location. To accomplish such three-dimensional location, typical prior art stands for scintillation detectors utilize a number of linear motions to move the detector to the desired position. Typically, nuclear camera stands comprise a vertical column to permit height adjustment of the detector. In addition, the vertical column is often provided on a mobile base to permit the equivalent of length and width adjustments. Sometimes the length or width adjustment is accomplished directly from the vertical beam by means of extendable arms which, together with the detector, can be moved up or down the vertical beam. In some progressive stands, the vertical beam is further provided with a pivotal yoke on which the camera may be tilted from a horizontal or other fixed orientation. All such stands, however, use to a greater or lesser degree, rectilinear coordinate geometry. Thus, it typically takes an operator three steps to move the detector to the desired location and orientation with respect to the patient. In addition, such movements typically require the use of a power mechanism for assistance.

The subject invention recognizes that the use of polar coordinates makes the positioning of the detector a simpler and more efficient task with less inconvenience to the patient. Given a sphere in free space surrounding a portion of the patient to be examined, the detector can be easily and quickly positioned to the desired location with a maximum of two steps which can be done in unison. In terms of polar coordinates, the inventive apparatus permits adjustment along the two angular displacements which uniquely define a point on a sphere of a given radius.

SUMMARY OF THE INVENTION

Applicants have discovered a curved beam apparatus for use as a scintillation detector stand which permits easy and efficient positioning of a scintillation detector in a convenient location with respect to a patient for clinical study including static studies, tomographic studies, and dynamic, such as whole body, studies. In two manually controlled rotational movements, the scintillation detector is moved into the desired location without the need to disturb the patient.

In a preferred embodiment, the curved beam apparatus for supporting and manually positioning a scintillation detector to a desired position on a hypothetical sphere surrounding a portion of a patient comprises a generally C-shaped support member. The scintillation detector is pivotally attached to one end of the support member. The apparatus further comprises a carrier member which slidably engages the support member to retain the support member and to permit relatively low frictional orbital movement of the support member along a predetermined planar arcuate path defined by the shape of the support member. To permit manual movement of the support member, the apparatus further comprises means, such as a counterweight, mounted at the other end of the C-shaped support member chordally opposed to the scintillation detector. This counterbalancing of the scintillation detector permits the support member to retain relatively fixed a position to which it might be moved relative to the carrier member. Finally, the curved beam apparatus also comprises a base member for rotatably supporting said carrier member and for permitting the carrier member and hence the support member axial rotation.

Several techniques are disclosed for permitting a smooth relative rotational sliding movement between the C-shaped support member which is preferably circular and the carrier member which supports it. In a preferred embodiment, either side of the support member includes a rail preferably made of steel whose curvature corresponds to the curvature of the support member as well as the curvature of inner portions of the carrier member wherein it rotates. Correspondingly, the carrier member includes a circular groove configured and dimensioned to accomodate the passage therethrough of the rails of the support member. Within the circular groove, the carrier member is provided with a plurality of cam followers which engage the steel rails of the support member regardless of either the position of the support member with respect to the carrier member or the rotational orientation of the carrier member with respect to the base member.

BRIEF DESCRIPTION OF THE DRAWINGS

FIG. 12 is a diagrammatic perspective view of the curved beam apparatus shown in FIG. 1 together with a patient table for static and dynamic studies.

DETAILED DESCRIPTION OF THE INVENTION

Figure 1:
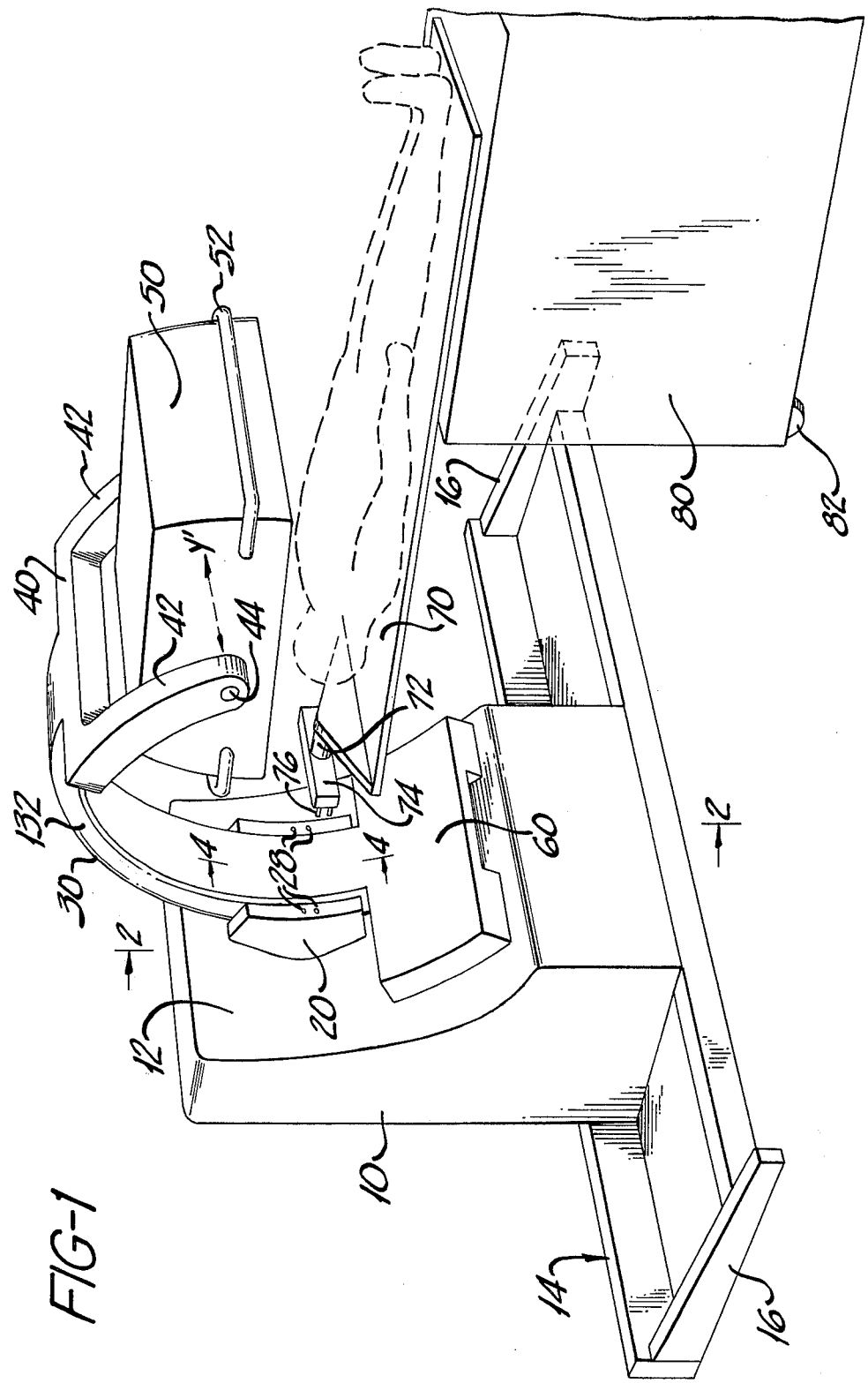
FIG. 1 is a diagrammatic perspective view of a curved beam apparatus according to the present invention together with a patient table for static and tomographic studies.

Referring first to FIG. 1, there is shown a scintillation detector supported by the inventive curved beam apparatus or scintillation detector stand. The curved beam apparatus comprises a base member 10 which has a generally cubic appearance except for a curved frontal portion 12. For static and tomographic studies the base member 10 is stationary. Alternatively, if a dynamic study is desired, see FIG. 12, base member 10 may be moved along a lateral support 14 along axis Y transverse to the orientation of a patient. Where space is at a premium, or alternatively if dynamic studies are not desired, the base member 10 may be placed directly on a floor surface without utilization of a lateral support 14. In such an embodiment, base member 10 would be provided with a leg along either edge thereof protruding forward of its frontal portion 12 in much the same manner as do legs 16 of lateral support 14. Both the base member 10 and lateral support 14 have flat rear surfaces to permit their being placed directly against a wall to further minimize space requirements.

Attached to the front portion 12 of base member 10 is a carrier member 20. As shown in greater detail in FIG. 4, carrier member 20 is attached to base member 10 by means of a circular pivot bearing mechanism 24 positioned about opening 22. By means of pivot bearing mechanism 24, the carrier member 20 is rotatable about an axis X perpendicularly intersecting the center of opening 22. Carrier member 20 is arcuate and has a wide central groove therein for engaging a C-shaped support member or C-arm 30.

C-arm 30 defines a segment of a circle of radius r and is permitted to move within carrier 20 along the circumference of said circle. Relative to the center of said circle, the movement of C-arm 30 can be considered orbital. As further shown in FIG. 1, there is provided at one end of C-arm 30 a yoke 40 which conveniently may have, though not necessarily, the same circular orientation as does the C-arm 30. Near the end of either fork 42 of yoke 40 is a ball bearing 44 to which a scintillation detector 50 is pivotally attached. By means of the pivotal attachment of the scintillation detector 50 to yoke 40, the detector may be tilted in a pivotal manner independent of either the orbital movement or the rotation of C-arm 30. This pivotal movement is about an axis Y' intersecting the centers of the two ball bearings 44.

Attached to the other end of C-arm 30 is a counterweight 60 which functions to assure that the orbital orientation of C-arm 30 remains fixed in relation to carrier member 20 at any desired point along the arcuate path between said carrier member 20 and C-arm 30. Counterweight 60 permits manual orientation of the scintillation detector 50 to any point along the circle defined by said C-arm 30. Counterweight 60 defines one end of the permitted rotational movement between the carrier member 20 and C-arm 30. Similarly, yoke 40 defines the other end of said rotational movement.

Figure 9:
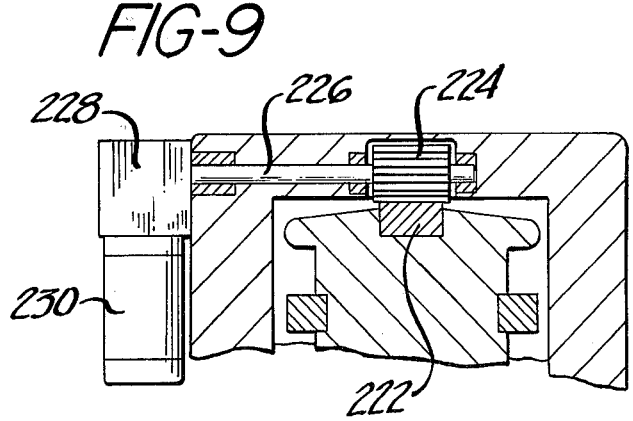
FIG. 9 is a view similar to FIG. 7 but including a drive mechanism in lieu of the counterweight as shown in the embodiment of FIG. 10.
Figure 10:
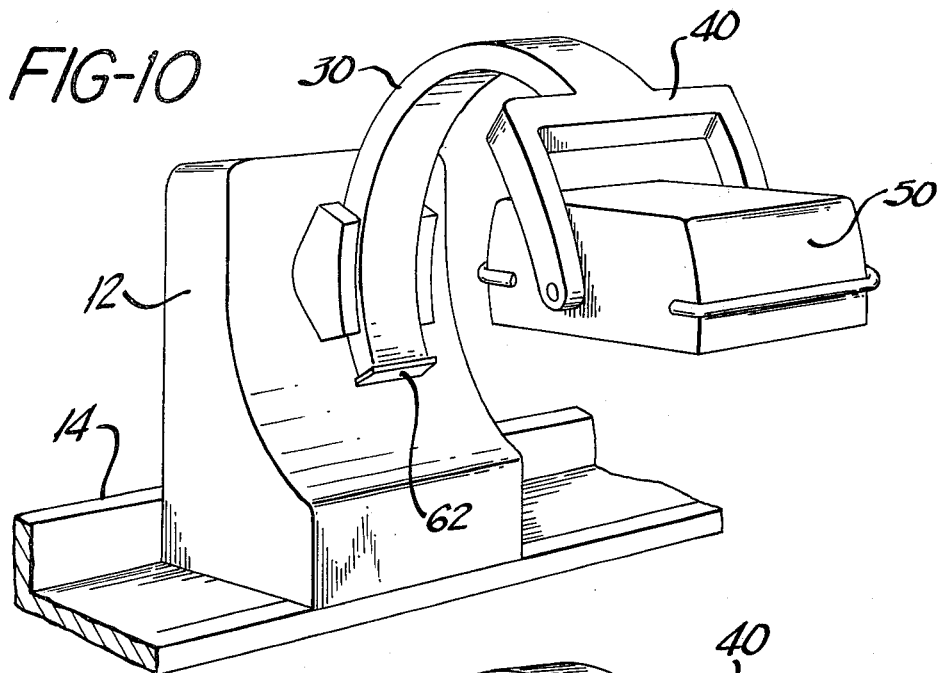
FIG. 10 is an alternate embodiment similar to FIG. 1 without a counterweight.

Alternatively, the counterweight 60 may be eliminated as shown in FIG. 10 if powered orbital movement is desired. If a counterweight 60 is not used, a stop 62 is attached to the free end of C-arm 30. The mechanism in connection with this alternate embodiment is described in detail below in connection with FIG. 9.

Figure 11:
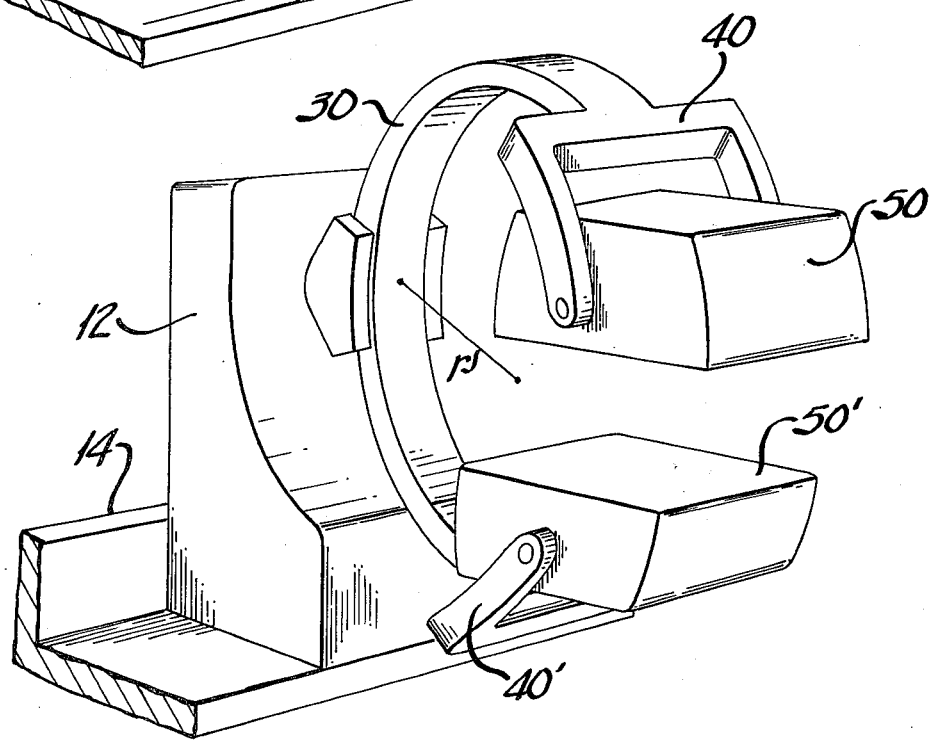
FIG. 11 is another alternate embodiment similar to FIG. 1 wherein the counterweight is replaced by a second scintillation detector.
Figure 1:
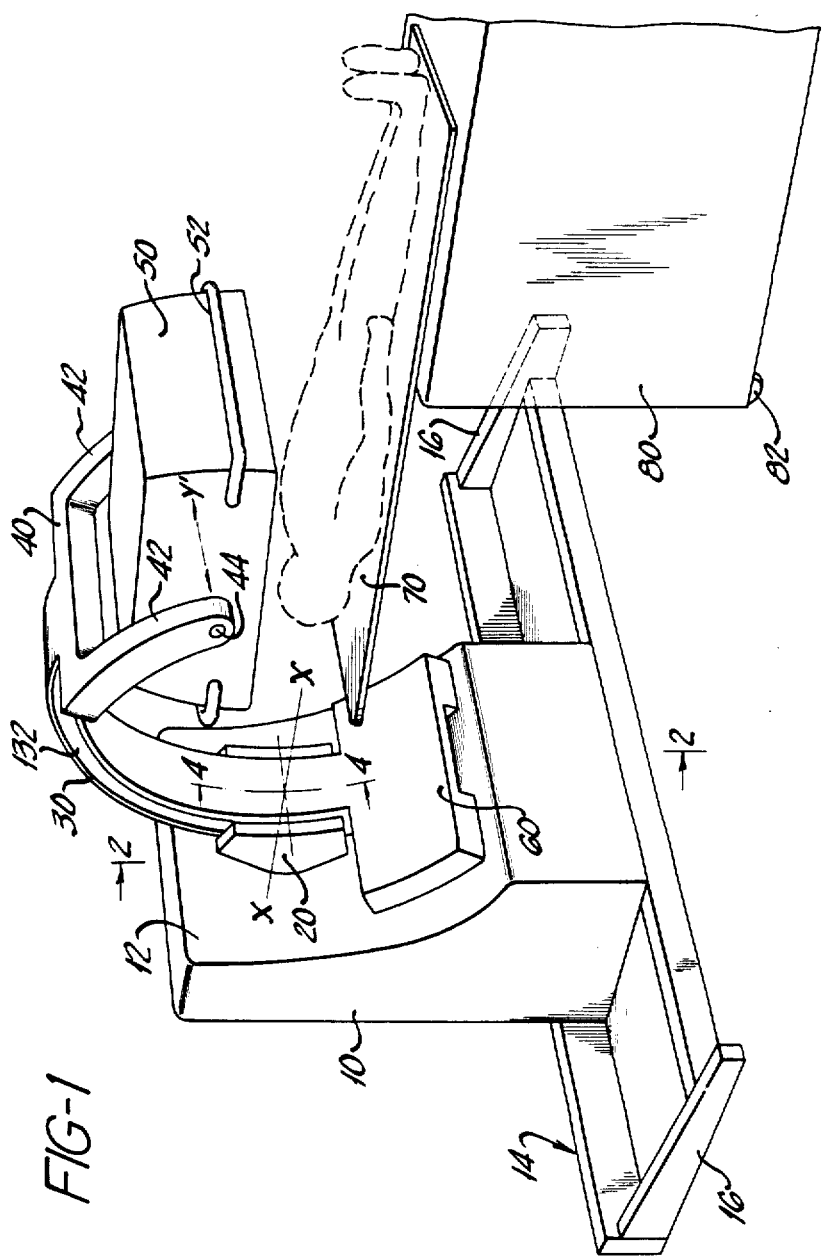

As a further alternative to counterweight 60, a second scintillation detector 50' may be utilized as shown in FIG. 11. The second scintillation detector 50', requires that the C-arm 30 have attached thereto a second yoke 40' at the other end thereof.

The combination of the rotatability of carrier member 20 about the X axis, together with the orbital movement of C-arm 30 along a circumferential path, permits the scintillation detector 50 to be positioned to any location about a hypothetical sphere of radius r within which a section of a patient can be conveniently located. In addition, the scintillation detector 50 once located to the desired region of said sphere can there be tilted along a plane substantially intersecting the surface of said sphere.

Figure 4:
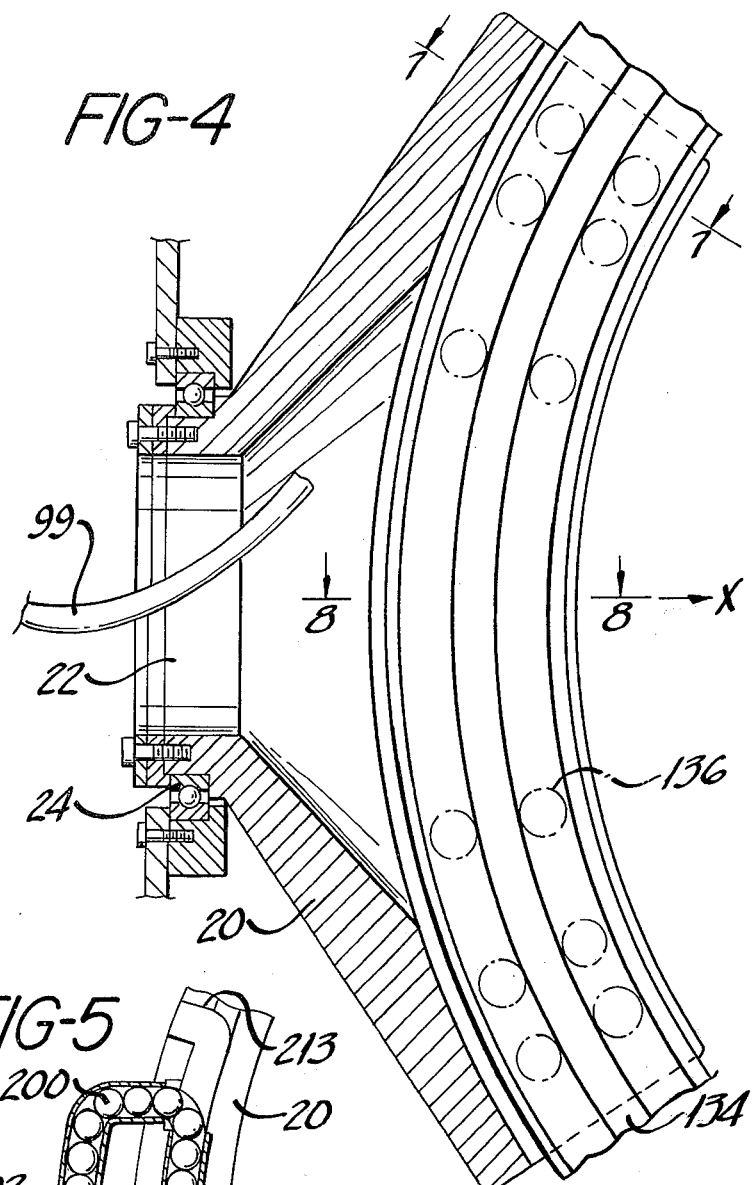
FIG. 4 is a section taken along line 4—4 of FIG. 1.
Figure 7:
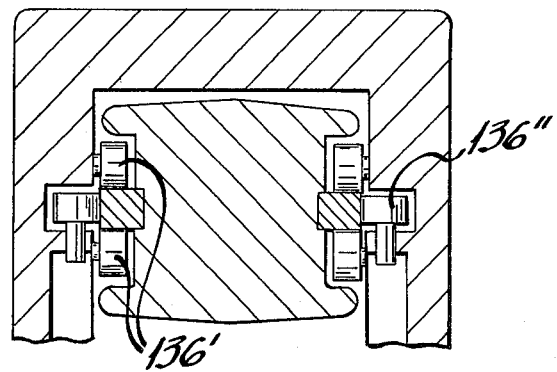
FIG. 7 is a section taken along line 7—7 of FIG. 4.

Describing now in greater detail the mechanism for permitting rotational movement between the C-arm 30 and the carrier member 20, refer now to FIG. 4. Either side of C-arm 30 has a groove 132 as shown in FIG. 1 running lengthwise thereof. In the center of both grooves 132 is a rail 134 which is preferably steel or some other hardened material. Steel rails 134 have the same curvature as C-arm 30. Carrier member 20 is provided with means for engaging both steel rails 134 of C-arm 30. In a preferred embodiment, the means for engaging steel rails 134 is a plurality of cam followers 136. Cam followers 136 include opposed pairs of cam followers 136' on either side of steel rail 134 for engaging said steel rail 134 during all non-horizontal orientations of said C-arm 30. In addition to opposed pairs of cam followers 136', the carrier member 20 is further provided with lateral cam followers 136" shown in FIG. 7 which engage the top edge of rail 134 whenever said C-arm 30 is in a non-vertical orientation. Either steel rail 134 may variously be engaged by six pairs of opposed cam followers 136' or two lateral cam followers 136". As carrier member 20 is rotated away from its normal vertical position as shown in FIG. 1, an increased reliance is placed on lateral cam followers 136" as the carrier member approaches a generally horizontal orientation. The C-arm 30 is structured to minimize and equalize deflection due to the weight of the scintillation detector 50 and counterweight 60 regardless of the orientation of the C-arm 30. Cam followers 136 resist the bending and torsional forces forces generated by the weight of the scintillation detector 50, C-arm 30 including yoke 40, and counterweight 60.

With counterweight 60 utilized, the apparatus is balanced at any orientation. However, to assure that no undesired external force alters the preselected orientation of the scintillation detector 50, a brake mechanism is provided for the movement of C-arm 30, for axial rotation of carrier member 20, and for tilting scintillation detector 50. The brake mechanisms are selectively controllable by the operator to permit one or more of these functions by squeezing a hand control bar 52 which is provided at either end of the scintillation detector 50. Moreover, unless an operator squeezes a control bar 52, all brakes are on. Thus, manual reorientation of the detector is begun by squeezing one of the control bars 52 which removes the brake engagement.

Figure 2:
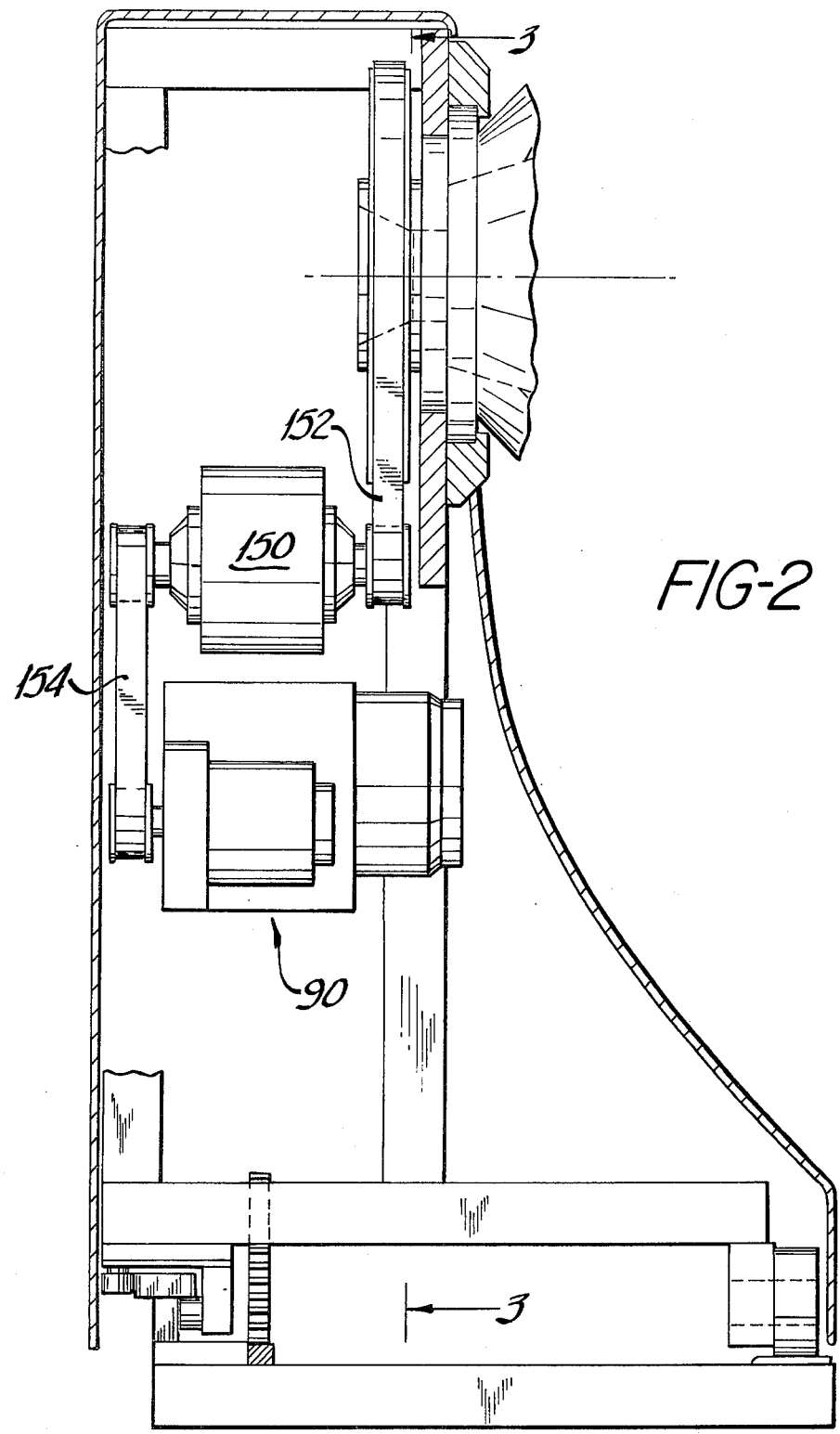
FIG. 2 is a section taken along line 2—2 of FIG. 1.
Figure 3:
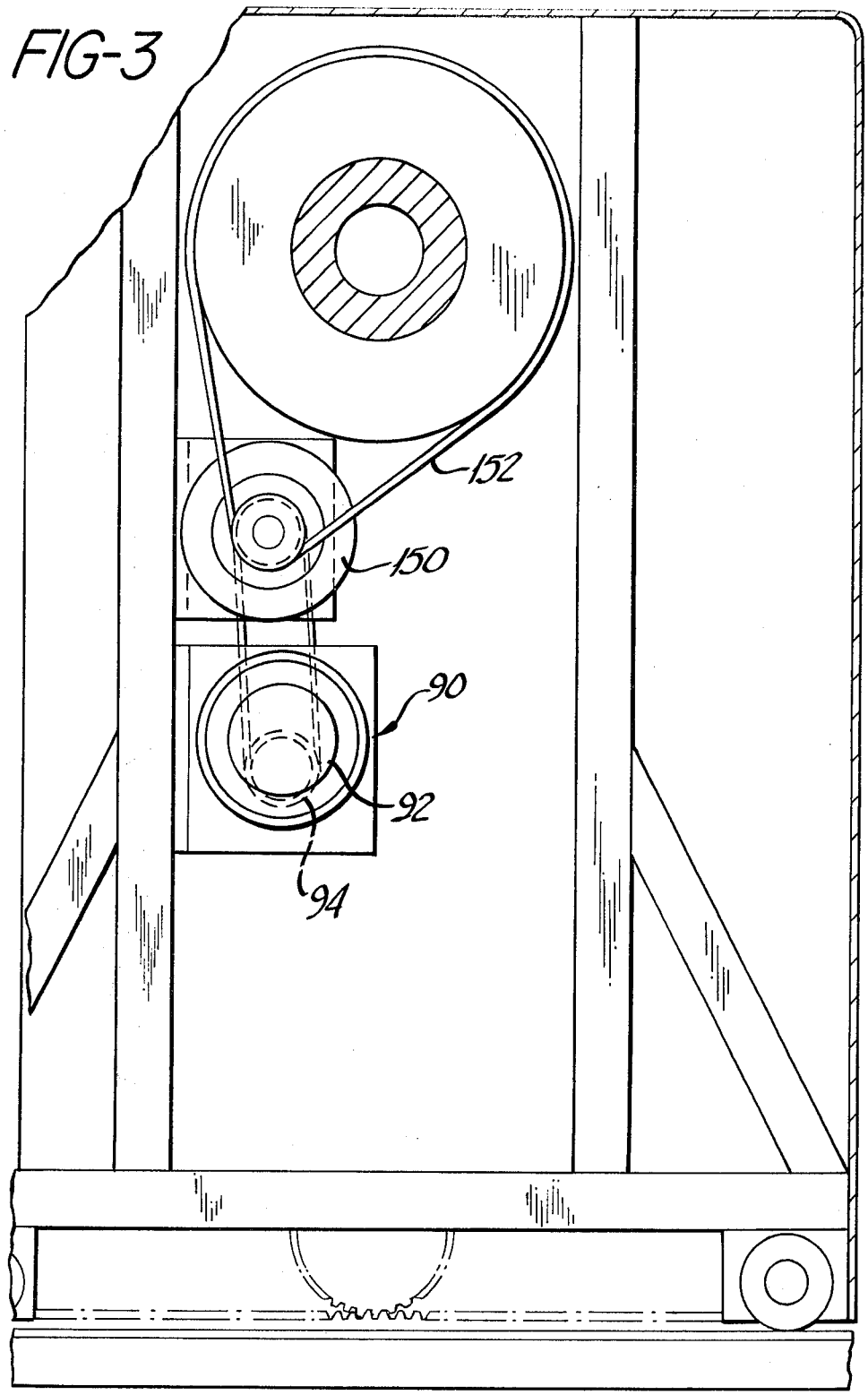
FIG. 3 is a section taken along line 3—3 of FIG. 2.
Figure 8:
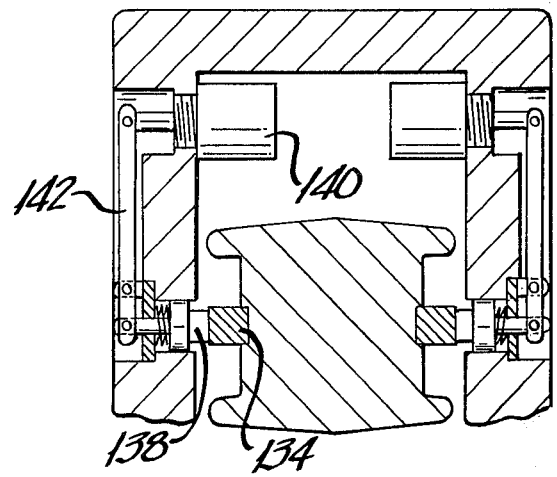
FIG. 8 is a section taken along line 8—8 of FIG. 4.

The braking action on C-arm 30 by carrier member 20 is provided by spring loaded friction pads 138 shown in FIG. 8. Except when deactivated, spring loaded friction pads 138 bear against rails 134 to restrain movement thereof relative to carrier member 20. The spring loaded friction pad 138 is remotely controlled by a solenoid 140 through linkage 142. Rotation of carrier member 20 is restrained by a brake assembly 150 disposed within base member 10 as shown in FIGS. 2 and 3. Brake assembly 150, is connected to the carrier member 20 by means of a first timing pulley and belt 152.

Several alternate methods of translating, supporting, and guiding the C-arm 30 with respect to the carrier member 20 are contemplated. For instance, the carrier member 20 can be devoid of any cam followers 136, and merely engage rails 134 in a groove dimensioned and configured for that purpose. In such an arrangement the groove within carrier member 20 is lined with a metal such as bronze to create a low coefficient of friction between the groove of the carrier member 20 and the steel rail 134. Additionally, a low friction surface treatment of steel rails 134 as well as of the bronze lined groove of carrier member 20 further aids in the ease with which the C-arm 30 can be slid or translated therethrough.

Figure 5:
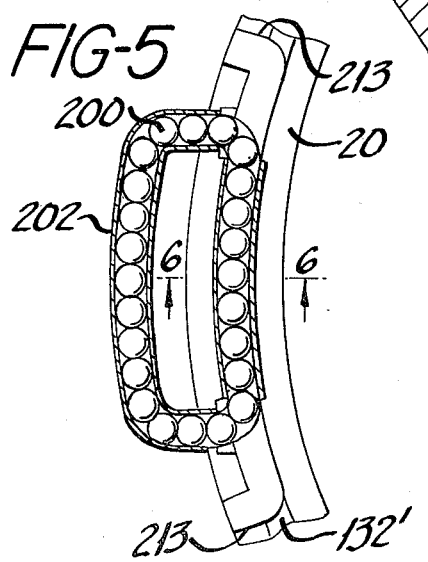
FIG. 5 is a section of an alternate embodiment similar to FIG. 4 showing a section of the carrier member which includes a recirculating ball mechanism within the carrier.
Figure 6:
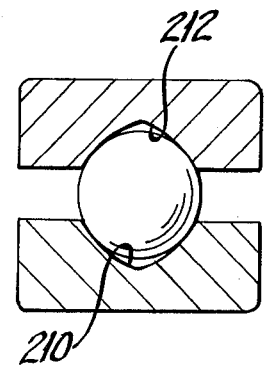
FIG. 6 is a section taken along line 6—6 of FIG. 5.

FIG. 5 shows a yet other alternative embodiment for the engagement of the C-arm 30 by carrier member 20. In this embodiment, cam followers 136 are replaced by a plurality of recirculating metal balls 200 which are disposed within a recirculating tube 202. The recirculating tube 202 is housed within the carrier member 20 so that only a portion of the balls 200 are exposed. The exposed portion of balls 200 is sufficient to permit convenient translation of groove or raceway 132' of the C-arm 30. The balls 200 are confined under a preload to minimize free play of C-arm 30. In this arrangement the groove 132' of C-arm 30 has a track 210 as shown in FIG. 5 along which the balls freely roll. Opposing track 210 is a track 212 housed within the carrier 20. Both tracks 210 and 212 have an arch-like cross-sectional design configured to contain the balls 200 as shown in FIG. 6. The track 212 in carrier member 20 is terminated at both ends by solid deflectors 213 which direct the balls 200 upward into the recirculating tube 202 which is secured to the carrier member 20.

Under any of the above described alternative embodiments that utilize a counterweight 60, positioning and orientation of the scintillation detector 50 can be done by unaided human strength but could be powered by electromagnetic, electromechanical, or fluid power means. In addition, devices such as gear or belt trains can be used to provide mechanical advantage to human strength.

If desired, the counterweight 60 could be eliminated; however, this requires alternative means for driving the C-arm 30. As shown in FIG. 9, the means for driving C-arm 30 can be accomplished by a rack 222 and pinion 224. Both the rack 222 and pinion 224 are provided with enmeshing teeth. The pinion 224 is driven through shaft 226 by a gear box 228 attached to a motor 230. While this technique is generally not as desirable as the use of a counterweight 60, the technique has advantages, particularly when a relatively heavy scintillation detector is to be utilized.

As shown in FIG. 11 and discussed briefly above, the counterweight 60 may be replaced by a second scintillation detector hung on a second yoke 40', so long as the weight of the second scintillation detector 50' is comparable to the weight of the first scintillation detector 50. One use of this arrangement would be to provide two different types of scintillation detectors in one apparatus. For instance, if one scintillation detector is a wide field of view, the second scintillation detector may be a small field of view or a high resolution detector for cardiac imaging and emission computed tomography of the brain. Alternatively, the two mounted detectors may be identical. Under such an arrangement the apparatus would have the ability to perform simultaneous anterior and posterior whole body scans and to collect data at twice the rate which is advantageous, for instance, in emission computed tomographic studies.

Alternatively, the counterweight 60 opposing the scintillation detector 50 could be replaced with a secondary imaging or non-imaging scintillation detector 50' for acquiring the 180° conicidence protons from positron emitting isotopes in emitted computed tomography studies. The primary detector 50 would be collimated with either a parallel hole collimator or a converging collimator focused at the second detector. In that case, the secondary scintillation detector 50' would not be an imaging device but merely an event detector, used to discriminate out scattered events.

Alternatively, both detectors 50 and 50' could be imaging detectors and neither would be collimated. The imaging process would be by means of event time conicidences in each detector, which would require considerably faster detectors than that currently used, such as intrinsic sodium iodide.

In connection with any combination of embodiments described above, the carrier member 20 and yoke 40 are open centered to permit enclosed passage of an electrical conductor 99 from a remote power source to the scintillation detector 50. By means of this expedient, no wiring ever need get in the way of either the operator or the patient.

FIG. 3 further shows a drive motor and clutch assembly generally designated as 90 for use in tomographic studies, i.e. when it is desired to have the scintillation detector 50 rotate about the X—X axis as shown in FIG. 1. Assembly 90 includes a clutch 92 by which drive motor 94 may be engaged. Engagement is accomplished by a second timing pulley and belt 154 which connects brake assembly 150 with drive motor and clutch assembly 90. For such tomographic studies, the assembly 90 includes an encoder with which rotational movement of said scintillation detector 50 may be programmed. The apparatus may be programmed to start and stop at any given series of positions along the rotational orbit. Typically, in a tomographic study the carrier will rotate in excess of 360° to permit the detector to fully orbit the patient and acquire sufficient information to permit a planar reconstruction of the patient being diagnosed. The excess rotation permits some overlap to ensure sufficient information acquisition throughout.

The patient being diagnosed is placed on cantilevered patient support 70 which is slideably secured to patient table 80. The axis of the portion of the patient's head or body under study is aligned visually into proper relationship with the axis of rotation of the carrier member 20. Patient table 80 has casters 82 and vertical adjustment capability (not shown) which in combination with the slideably mounted patient support 70 permits easy and accurate patient positioning. The cantilevered construction of patient support 70 permits the scintillation detector 50 to orbit about the patient's body or head while minimizing the air gap through which radiation must travel. Of course, static studies may also be carried out with this arrangement.

For dynamic studies, see FIG. 12, such as whole body studies, the scintillation detector 50 and the entire curved beam apparatus translates parallel to the patient along the Y axis. The patient being diagnosed is placed on patient table 80' which is provided with wheels 82' whereby the patient may be moved easily into the proper location for diagnosis. The patient table 80' may be adjusted vertically by means not shown to permit the scintillation detector 50 to follow the patient's body contour as closely as possible. Static studies may also be done using table 80'.

Implicit in the discussion of all of the above discussed embodiments is a specific radius of curvature of C-arm 30, which of course predetermines the radius of the spherical movement that the C-arm 30 in combination with the rotational ability of carrier 20 is capable of with respect to a specified central point. In order to shorten or augment this radius without changing the C-arm 30, yoke 40 may be pivotally attached to C-arm 30. This would permit the scintillation detector 50 mounted on a C-arm 30 of a given fixed curvature to be brought closer or alternatively further away from the patient, as may be desired.

We claim:

1. A support structure for supporting and positioning a scintillation detector to a desirable location relative to a patient which comprises:
   (a) a generally C-shaped support member having a yoke for pivotally supporting said scintillation detector at one end portion thereof to permit said detector to pivot about a first axis defined by said yoke;
   (b) a carrier member engaging said support member and for permitting orbital movement of said support member along a predetermined planar arcuate path transverse to said first axis and defined by the shape of said support member such that said scintillation detector is displaced relative to said carrier member during orbital movement of said support member;
   (c) means for orbiting said support member along said arcuate path; and
   (d) a base member rotatably supporting said carrier member and for permitting said carrier member and hence said support member axial rotation about a second axis orthogonal to said first axis such that said support member remains fixed relative to said carrier member during axial rotation of said support member.

2. A support structure according to claim 1 wherein said means for orbiting said support member along said arcuate path includes a rack and pinion disposed within said carrier member.

3. A curved beam apparatus for supporting and manually positioning a scintilliation detector to a desired position relative to a patient which comprises:
   (a) a generally arcuate support member including means for pivotally supporting about a first axis the scintillation detector at one end portion thereof;
   (b) a carrier member engaging said support member for retaining said support member and for permitting relatively low friction orbital movement of said support member along a predetermined arcuate path transverse to said first axis;
   (c) means for moving said support member along said arcuate path;
   (d) means disposed at another end portion of said arcuate support member chordally opposed to said scintillation detector for counterbalancing said scintillation detector, thus permitting said support member to retain a relatively fixed position to which it is moved with respect to said carrier member; and
   (e) a base member for rotatably supporting said carrier member and for permitting said carrier and hence said support member axial rotation about a second axis orthogonal to said first axis.

4. A curved beam apparatus according to claim 3 wherein said means for pivotally supporting said scintillation detector at one end of said support member includes a yoke extending from one end of said support member.

5. A curved beam apparatus according to claim 4 wherein said pivot support means further includes a bearing at either end of said yoke.

6. A curved beam apparatus according to claim 4 wherein said carrier member has an opening therethrough for the passage therethrough of a conductor for electrical connection between said scintillation detector and a remote source of power and wherein said yoke is open centered to permit said conductor to be connected to a scintillation detector directly through said pivot support means.

7. A curved beam apparatus according to claim 3 wherein said C-shaped support member is circular, the arcuate path of said support member is circumferential such that the combination of the orbital movement of said support member and the axial rotation of said carrier member by said base member permits spherical positioning of the scintillation detector.

8. A curved beam apparatus according to either of claim 3 or 7 wherein said base member includes a bearing mechanism for permitting 360 degrees of axial rotation of said carrier member.

9. A curved beam apparatus according to claim 3 wherein said base member includes means for lateral motion.

10. A curved beam apparatus according to claim 3 wherein said support member further includes a rail along portions of either side thereof for engaging inner portions of said carrier member.

11. A curved beam apparatus according to claim 10 wherein said carrier member includes a plurality of cam followers adapted for engaging the rails of said support member.

12. A curved beam apparatus according to any of claim 8, 9, or 10 wherein said carrier member further includes means for restraining orbital movement of said support member.

13. A curved beam apparatus according to claim 12 wherein said restraining means comprises spring loaded friction pads adapted for bearing on the rails of said support member.

14. A curved beam apparatus according to claim 10 wherein said rails are of a first metal and inner portions of said carrier member for engaging said rails are of a second metal dissimilar from said first metal so as to provide a relatively low coefficient of friction therebetween during orbital movement of said support member.

15. A curved beam apparatus according to claim 10 wherein said carrier member includes a recirculating ball mechanism for engaging the rails of said support member.

16. A curved beam apparatus for mounting thereon a scintillation detector adapted for emission computed tomographic studies which comprises:
   (a) a counterbalanced subassembly including means for moving the scintillation detector to a spherical coordinate on the surface of an imaginary sphere surrounding a portion of a patient to be examined;
   (b) a relatively upright, generally cubic, base member for supporting said subassembly, said base member having a curved frontal portion; and
   (c) means for attaching said subassembly to said base member in a manner to permit the scintillation detector to be moved to any desired location on said sphere without traversing the free space within the sphere where the patient is located wherein said entire subassembly protrudes from the frontal portion of said base member.

17. A counterbalanced structure for a scintillation camera having a detector adapted for emission computed axial tomography of a patient comprising:
   (a) a base member;
   (b) a carrier member rotatably supported by said base member for rotating said carrier member about a first axis;
   (c) a support arm defining a circumferential section of an arcuate path which intersects said first axis, said support arm disposed for slidable engagement within said carrier member such that said support arm is adapted for both axial rotation jointly with said carrier member about said first axis and for orbital motion relative to a fixed carrier member along the path defined by said circumferential section; and
   (d) means for pivotally mounting the detector at one end portion of said support arm to permit said detector to pivot about a second axis, whereby rotation of said carrier member results in said detector being axially rotated about said first axis between said mounting means and said first axis at a constant radius and further whereby orbital displacement of said support arm alters said radius.

* * * * *

UNITED STATES PATENT AND TRADEMARK OFFICE
CERTIFICATE OF CORRECTION

PATENT NO. : 4,426,578

DATED : January 17, 1984

INVENTOR(S) : James M. Bradcovich, et al

It is certified that error appears in the above-indentified patent and that said Letters Patent is hereby corrected as shown below:

In the Drawings:

Replace Fig. 1 with the attached Fig. 1.

Add the attached Fig. 12.

Signed and Sealed this

Eighth Day of June, 1993

Attest:

MICHAEL K. KIRK

Attesting Officer

Acting Commissioner of Patents and Trademarks